(12) United States Patent
Maynes et al.

(10) Patent No.: US 11,160,700 B1
(45) Date of Patent: Nov. 2, 2021

(54) APPARATUS, SYSTEM, AND METHOD FOR COVERING A MEDICAL CAST WITH A REMOVABLE PROTECTIVE STRUCTURE

(71) Applicants: Erica Maynes, Marana, AZ (US); Abhay Sanan, Tucson, AZ (US)

(72) Inventors: Erica Maynes, Marana, AZ (US); Abhay Sanan, Tucson, AZ (US)

(*) Notice: Subject to any disclaimer, the term of this patent is extended or adjusted under 35 U.S.C. 154(b) by 706 days.

(21) Appl. No.: 15/909,426

(22) Filed: Mar. 1, 2018

Related U.S. Application Data

(60) Provisional application No. 62/465,497, filed on Mar. 1, 2017.

(51) Int. Cl.
*A61F 15/00* (2006.01)
*A61F 13/04* (2006.01)

(52) U.S. Cl.
CPC .......... *A61F 15/004* (2013.01); *A61F 15/008* (2013.01); *A61F 13/041* (2013.01)

(58) Field of Classification Search
CPC .... A61F 15/004; A61F 15/008; A61F 13/041; A61F 13/08; A41D 17/00; A41D 17/005; A41D 17/02; A41D 27/12; A41D 27/14; A41D 27/16; A41B 3/18; A41B 7/00; A41B 7/04; A41B 7/06; A41B 7/08; A41B 7/12; A41B 11/10
USPC ........................ 602/3; 36/1.5, 2 R; 2/59–61
See application file for complete search history.

(56) References Cited

U.S. PATENT DOCUMENTS

| | | | | |
|---|---|---|---|---|
| 1,712,035 A | * | 5/1929 | Frykman | A43B 3/02 |
| | | | | 36/1.5 |
| 2,956,561 A | | 10/1960 | Houde | 128/83.5 |
| 3,329,143 A | | 7/1967 | Gordon | 128/82 |
| 3,416,518 A | | 12/1968 | Samuels | 128/82 |
| 3,741,203 A | | 6/1973 | Liman | 128/82 |
| 4,043,326 A | | 8/1977 | Little et al. | 128/82 |
| 4,254,765 A | | 3/1981 | Brown et al. | 128/82 |
| 4,646,727 A | | 3/1987 | Chambers | 128/82 |
| 4,986,265 A | | 1/1991 | Caponi | 128/82 |
| 5,063,919 A | | 11/1991 | Silverberg | 128/82 |
| 5,643,183 A | | 7/1997 | Hill | 602/3 |
| 5,720,712 A | | 2/1998 | Joy et al. | 602/3 |
| 6,053,882 A | | 4/2000 | Johansen | 602/14 |
| 6,298,496 B1 | | 10/2001 | Evans | 2/239 |
| 6,916,301 B1 | | 7/2005 | Clare | 602/3 |
| 7,066,899 B2 | | 6/2006 | Baron | 602/3 |
| 7,762,968 B1 | | 7/2010 | Hewitt | 602/3 |

(Continued)

*Primary Examiner* — Keri J Nelson
(74) *Attorney, Agent, or Firm* — Hayes Soloway P.C.

(57) ABSTRACT

A medical cast protective structure apparatus and methods are used to protect against unsanitary contamination of a medical cast. A medical cast has a hardened exterior layer and a plush interior layer. A water-resistant fabric cover has a substantially cylindrical shape and is positioned over at least a portion of an exterior of the medical cast and a terminating end of the medical cast. An annular pocket is formed in a first end of the fabric cover, wherein the first end of the fabric cover is positioned abutting the plush interior layer of the medical cast. A biasable clip is positioned within the annular pocket, wherein the biasable clip is movable between collapsed and expanded states, wherein in the expanded state, the annular pocket with biasable clip therein contacts the plush interior layer of the medical cast and is retained in a substantially stationary position relative to the medical cast.

16 Claims, 6 Drawing Sheets

(56) References Cited

U.S. PATENT DOCUMENTS

| | | | |
|---|---|---|---|
| 7,867,179 B2 | 1/2011 | Bindas | 602/3 |
| 8,382,691 B2 | 2/2013 | Rice | 602/3 |
| 8,430,829 B1 * | 4/2013 | Marchetti | A61F 15/00 602/3 |
| 2003/0191419 A1 | 10/2003 | Melin et al. | 602/3 |
| 2006/0287623 A1 * | 12/2006 | Beck | A61F 13/043 602/3 |
| 2012/0215144 A1 | 8/2012 | Rice | 602/3 |
| 2012/0323153 A1 | 12/2012 | Ferenc et al. | 602/3 |
| 2013/0096474 A1 | 4/2013 | Sager | 602/3 |
| 2014/0005582 A1 | 1/2014 | Dickinson | 602/3 |
| 2016/0136000 A1 | 5/2016 | Gaffney | A61F 13/041 |

\* cited by examiner

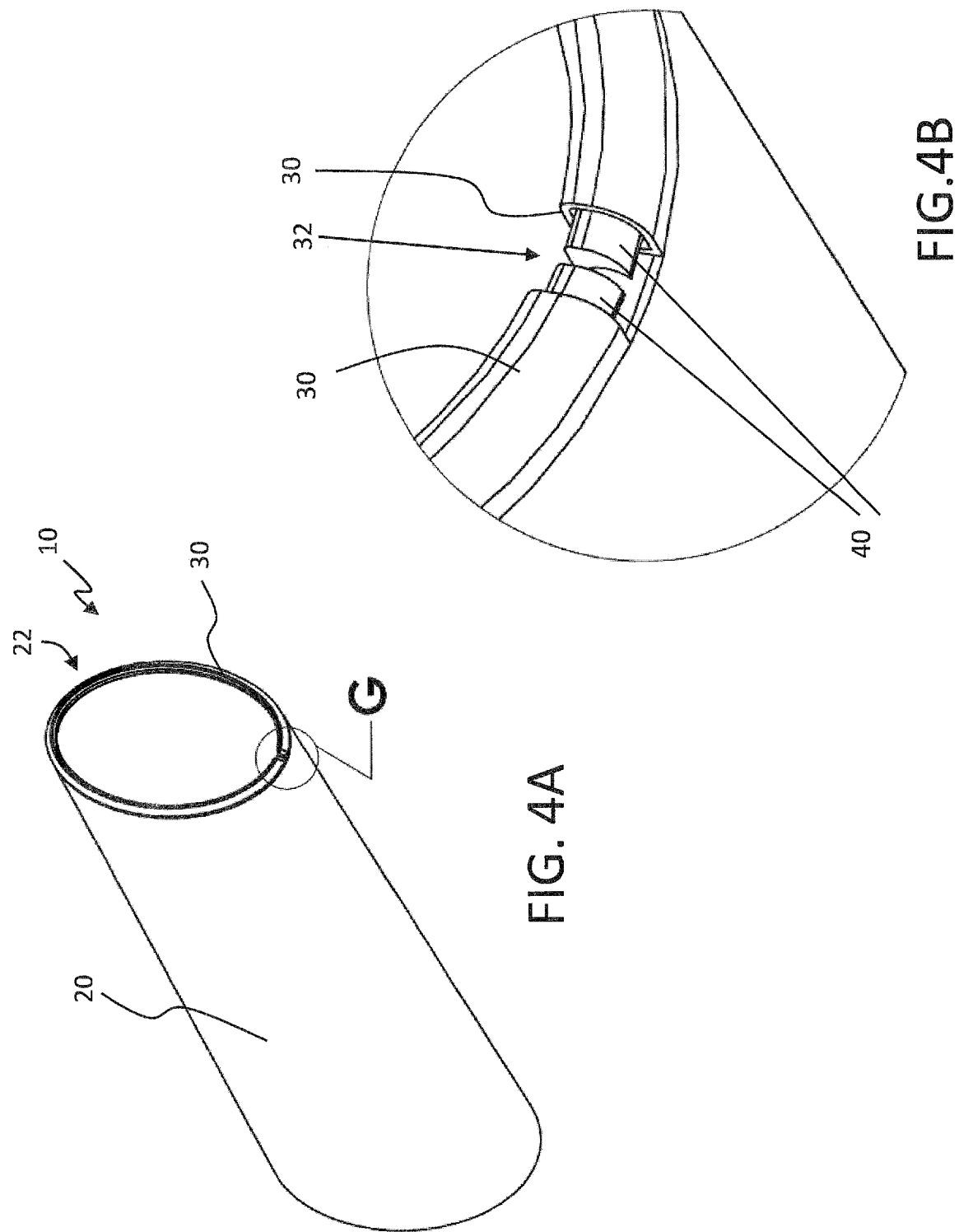

APPARATUS, SYSTEM, AND METHOD FOR COVERING A MEDICAL CAST WITH A REMOVABLE PROTECTIVE STRUCTURE

CROSS REFERENCE TO RELATED APPLICATION

This application claims benefit of U.S. Provisional Application Ser. No. 62/465,497 entitled, "Apparatus, System, and Method for Covering a Medical Cast with a Removable Protective Structure" filed Mar. 1, 2017, the entire disclosure of which is incorporated herein by reference.

FIELD OF THE DISCLOSURE

The present disclosure is generally related to protectants for medical casts and more particularly is related to an apparatus, system, and method for covering a medical cast with a removable protective structure.

BACKGROUND OF THE DISCLOSURE

Within the medical field, casts are used to temporarily encase limbs to provide stabilization for the limb during healing. These casts may include orthopedic casts, plaster casts, surgical casts, or others, and they're commonly constructed from materials which can be applied to a patient's limb in a malleable state and then cured to a hardened state. These casts, which may be referred to generally as medical casts, may be formed from plaster bandages, knitted fiberglass bandages impregnated with polyurethane, or thermoplastic bandages, among other materials. Once hardened, it is undesirable for these materials to be exposed to moisture, since moisture can degrade strength of the medical cast, and lessen its effectiveness in stabilizing the patient's limb.

While the medical cast is encasing the patient's limb, it is exposed to the patient's environment. In particular, the medical cast is exposed to a number of substances which commonly come into contact with limbs, such as bacteria, dirt, dust, or other contaminants. Many of these substances are unsanitary, and therefore, undesirable to have contacting the medical cast, especially since it is largely impossible to clean the medical cast with water or other liquids like one can do with washing his or her hands. While there are some devices offered for covering a cast to prevent it from getting dirty or contaminated with undesirable materials, these covers are usually cumbersome and ineffective since they are merely laid over or wrapped around the cast.

Thus, a heretofore unaddressed need exists in the industry to address the aforementioned deficiencies and inadequacies.

SUMMARY OF THE DISCLOSURE

Embodiments of the present disclosure provide an apparatus, system, and method for a medical cast protective structure. Briefly described, in architecture, one embodiment of the apparatus, among others, can be implemented as follows. A medical cast has a hardened exterior layer and a plush interior layer. A water-resistant fabric cover has a substantially cylindrical shape and is positioned over at least a portion of an exterior of the medical cast and a terminating end of the medical cast. An annular pocket is formed in a first end of the fabric cover, wherein the first end of the fabric cover is positioned abutting the plush interior layer of the medical cast. A biasable clip is positioned within the annular pocket, wherein the biasable clip is movable between collapsed and expanded states, wherein in the expanded state, the annular pocket with biasable clip therein contacts the plush interior layer of the medical cast and is retained in a substantially stationary position relative to the medical cast.

The present disclosure can also be viewed as providing a medical cast protective structure apparatus. Briefly described, in architecture, one embodiment of the apparatus, among others, can be implemented as follows. A fabric cover has a substantially cylindrical shape. An annular pocket is formed in a first end of the fabric cover. A biasable clip is positionable within the annular pocket, wherein the annular pocket with the biasable clip positioned therein is insertable into an interior portion of a medical cast with the biasable clip in a collapsed state, wherein after insertion into the interior portion of the medical cast, the biasable clip expands to an expanded state to contact an inner surface of the medical cast, wherein the annular pocket with the biasable clip therein is retained in a substantially stationary position relative to the medical cast.

The present disclosure can also be viewed as providing a method for applying a protective cover to a medical cast. In this regard, one embodiment of such a method, among others, can be broadly summarized by the following steps: providing a fabric cover having a substantially cylindrical shape, the fabric cover having an annular pocket formed in a first end thereof; positioning a biasable clip within the annular pocket; moving the biasable clip into a collapsed state and inserting the first end of the fabric cover into an interior portion of a medical cast having a hardened exterior layer and a plush interior layer, whereby the first end of the fabric cover is positioned proximate to the plush interior layer of the medical cast; expanding the biasable clip to an expanded state, whereby the annular pocket with biasable clip therein contacts the plush interior layer of the medical cast and is retained in a substantially stationary position relative to the medical cast; and moving a second end of the fabric cover over the hardened exterior layer of the medical cast, whereby the fabric cover is positioned against at least a portion of the hardened exterior layer and a terminating end of the medical cast.

Other apparatus, systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 4A-4B are isometric view and detailed view illustrations, respectively, of the biasable clip within the annular pocket of the fabric cover of the medical cast protective structure apparatus, in accordance with the first exemplary embodiment of the present disclosure.

DETAILED DESCRIPTION

The subject disclosure is directed to an improvement in the field of medical cast covers which includes the use of a cover which is removably positionable over a medical cast to protect it from unsanitary contaminations, such as bacterial contaminations. The cover is capable of being secured to the medical cast during use and then removed from the medical cast as desired by the user, such as to allow for the cover to be replaced and/or cleaned.

Figure 1:
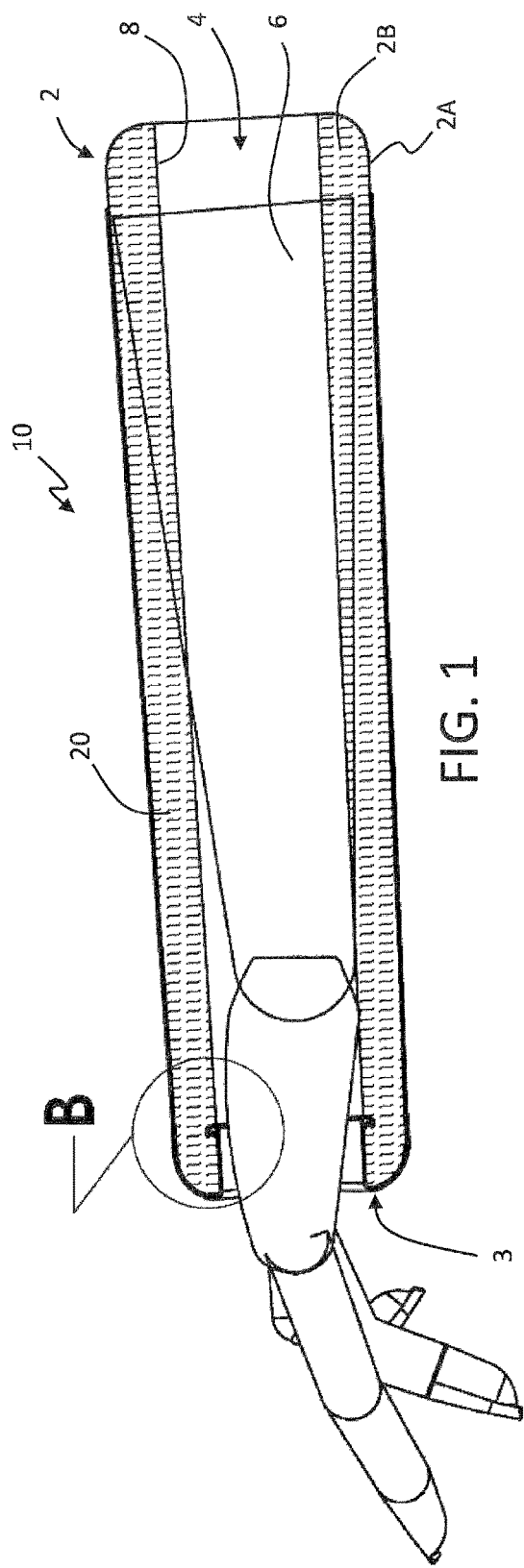
FIG. 1 is a cross-sectional view illustration of a medical cast protective structure apparatus, in accordance with a first exemplary embodiment of the present disclosure.
Figure 2:
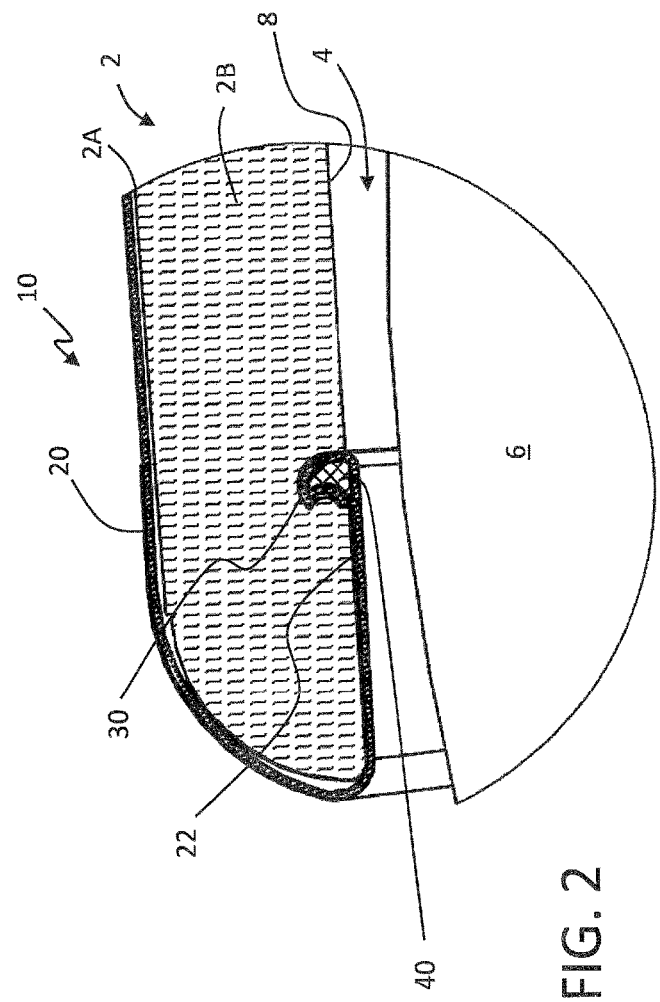
FIG. 2 is an enlarged, detailed, cross-sectional view illustration of portion B in FIG. 1 of the medical cast protective structure apparatus, in accordance with the first exemplary embodiment of the present disclosure.

FIG. 1 is a partial cross-sectional view illustration of a medical cast protective structure apparatus 10, in accordance with a first exemplary embodiment of the present disclosure. FIG. 2 is an enlarged, detailed, cross-sectional view illustration of portion B in FIG. 1 of the medical cast protective structure apparatus 10, in accordance with the first exemplary embodiment of the present disclosure. With reference to FIGS. 1-2, the medical cast protective structure apparatus 10, which may be referred simply as 'apparatus 10', has a water-resistant fabric cover 20 having a substantially cylindrical shape. An annular pocket 30 is formed in a first end 22 of the fabric cover 20. A biasable clip 40 is capable of being positioned within the annular pocket 30. The annular pocket 30 with the biasable clip 40 positioned therein is insertable into an interior portion 4 of a medical cast 2 with the biasable clip 40 in a collapsed state. After insertion into the interior portion 4 of the medical cast 2, the biasable clip 40 expands to an expanded state to contact an inner surface 8 of the medical cast 2, wherein the annular pocket 30 with the biasable clip 40 therein is retained in a substantially stationary position relative to the medical cast 2.

As shown in FIG. 1, the fabric cover 20 is positionable over the medical cast 2 along the exterior of the medical cast 2. Commonly, the medical cast 2 includes a rigid exterior surface 2A, such as one made from hardened fiberglass or plaster, and one or more plush interior layers 2B commonly formed from woven plush materials, such as cotton or synthetic padding. The rigid exterior layer 2A and plush interior layers 2B generally define an interior portion 4 of the medical cast 2 in which a limb 6 of the patient can be located, with the limb 6 of the patient substantially contacting the plush interior layers 2B while the rigid exterior layer 2A provides durable protection and rigidity to the limb 6. While all types of medical casts 2 may be used with the apparatus 10, it is described herein with reference to a medical cast 2 used with a human arm. In this example, as shown in FIG. 1, the medical cast 2 may be positioned over the patient's forearm (radius and ulna bones), the patient's wrist, and a portion of the patient's hand, where the medical cast 2 terminates at a forward location along the user's hand and at a rear location proximate to the patient's elbow. In other examples, the medical cast 2 may be a casting device positioned around other limbs or anatomy of a patient, human, animal, or otherwise.

The fabric cover 20 may have a substantially cylindrical design which is sized to fit over the medical cast 2 with the desired degree of snugness, ideally to allow the fabric cover 20 to remain in place along the exterior of the medical cast 2 with friction and/or elastic properties. For example, the fabric cover 20 may be constructed from a textile material with natural and/or synthetic materials, some or all of which include elastic materials. The overall length of the fabric cover 20 may be selected to fully cover the exterior surface of the medical cast 2, or as shown in FIG. 1, cover a portion of the exterior surface of the medical cast 2, such as a forward portion of the medical cast 2 along with a forward terminating end 3 of the medical cast 2. The fabric cover 20 may be manufactured from a variety of materials, but is preferably manufactured from materials that are water resistant and washable, such that the fabric cover 20 can act as a barrier to moisture gaining access to the medical cast 2 and be removed for cleaning as desired by the patient.

The positioning of the fabric cover 20 over the medical cast 2 includes the first end 22 of the fabric cover 20 being positioned along an interior surface 8 of the medical cast 2, as is shown in detail in FIG. 2. Specifically, the fabric cover 20 may be positioned from the rigid exterior material 2A of the medical cast 2 around a forward terminating edge 3, and at least partially within the interior cavity 4 formed by the medical cast 2. In this position, the first end 22 of the fabric cover 20 may be positioned between the inner surface 8 of the cast 2, e.g., against the exposed surface of the interior plush layers 2B, and the outer surface of the patient's limb 6. The first end 22 of the fabric cover 20 includes the annular pocket 30, which is retained within the interior portion of the medical cast 2 with the biasable clip 40 which can be biased into the plush interior layers 2B of the medical cast 2 to effectively retain the first end 22 of the fabric cover 20 within the interior portion of the medical cast 2.

The position of the biasable clip 40 and the annular pocket 30 in contact with the plush interior layer 2B of the medical cast 2 may include the annular pocket 30 being imbedded at least partially within the plush interior layer 2B of the medical cast 2, such that a substantial portion of the annular pocket 30 and biasable clip 40 are positioned interior of the exposed surface 8 of the interior push layer 2B. The degree to which the annular pocket 30 and biasable clip 40 are positioned within the interior plush layer 2B may depend on the plushness of the interior plush layer 2B, the force of expansion of the biasable clip 40, as well as other factors. While variations on the degree of contact exist, it is envisioned that the biasable clip 40 provides adequate force against the annular pocket 30 and into the interior plush layer 2B to retain the first end 22 of the fabric cover 20 in a substantially stationary position within the interior 4 of the medical cast 2.

Figure 3B:
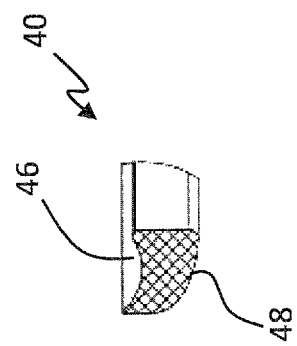
FIGS. 3A-3B are side view and cross-sectional view illustrations, respectively, of the biasable clip of the medical cast protective structure apparatus, in accordance with the first exemplary embodiment of the present disclosure.
Figure 3A:
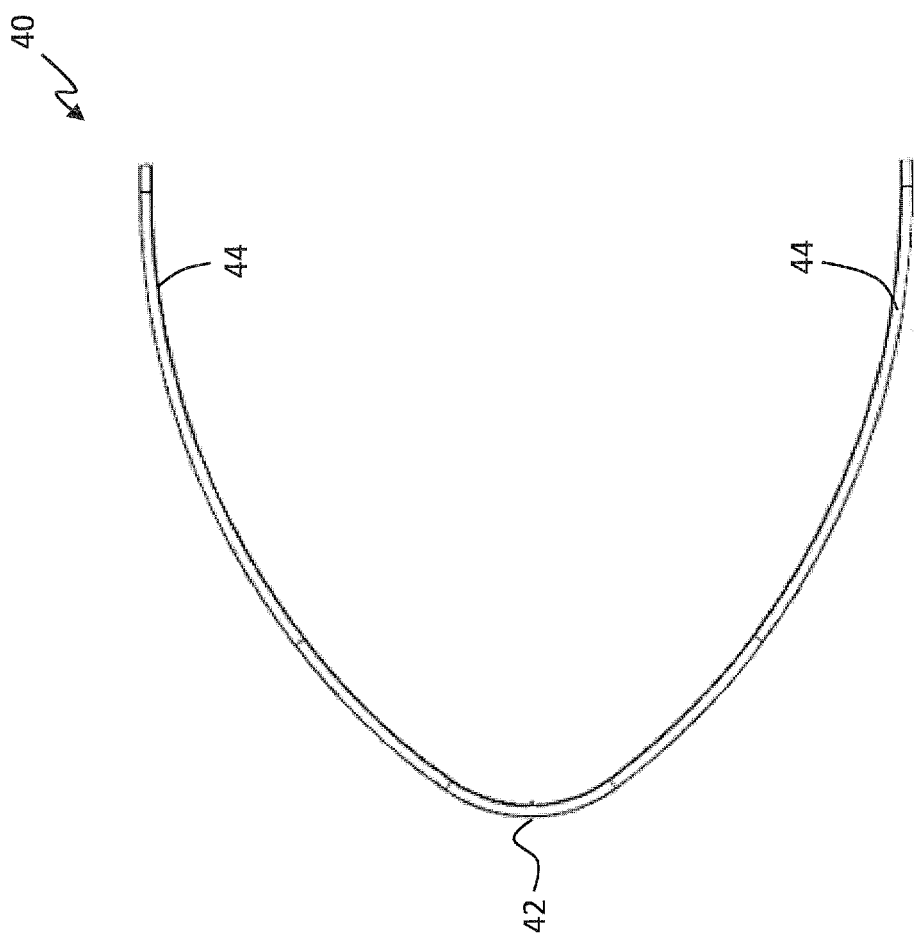

FIGS. 3A-3B are side view and cross-sectional view illustrations, respectively, of the biasable clip 40 of the medical cast protective structure apparatus 10, in accordance with the first exemplary embodiment of the present disclosure. The biasable clip 40 is designed to be positioned at least partially around the patient's limb within the medical cast, and as such, the biasable clip 40 may have a shape that conforms, at least partially, to the shape of the patient's limb.

For example, the biasable clip 40 may have a horseshoe or wishbone shape with a first section 42 having a small radius and two or more second sections 44 having larger radii, which may be designed to ergonomically match the anatomical shape of a human wrist or another anatomical location. While the dimensions may vary, in one example, the small radius and larger radii sizes may be as follows (dimensions in mm):

TABLE 1 exemplary clip radii dimensions

|  | Small Radius (mm) | Large Radii (mm) |
| --- | --- | --- |
| Child, small | 16 | 82-88 |
| Child, medium | 17 | 88-95 |
| Child, large | 18 | 96-103 |
| Child, extra large | 20 | 103-11 |
| Adult, small | 21 | 109-117 |
| Adult, medium | 24 | 123-133 |
| Adult, large | 25 | 130-140 |
| Adult, extra large | 26 | 136-147 |

The overall size of the biasable clip 40 may be designed to fit within the annular pocket of the fabric cover and/or the interior size of the medical cast. The biasable clip 40 can be cut or severed to conform its length to the intended use.

The biasable clip 40 may be constructed from a biasable material that allows it to flex and deform without breaking, and allows the biasable clip 40 to have a propensity to return to predetermined position after being biased. For example, the biasable clip 40 may have a natural (unbiased) shape as shown in FIG. 3A, where the natural tendency of the biasable clip 40 is to remain in that shape. When the biasable clip 40 is biased, such as by squeezing the second sections 44 towards one another, the second sections 44 may exert an outward force to return to the natural, unbiased shape. This natural, unbiased shape may be sized larger than the inner size of the plush material of the medical cast, such that when the biasable clip 40 moves from a biased or compressed shape into the natural, unbiased shape while positioned within the medical cast, the biasable clip 40 can exert an outwards force against the inner surface of the medical cast sufficient to hold the biasable clip 40 in place, which acts to frictionally hold the fabric cover in place. It is noted that the degree to which the biasable clip 40 can be biased, or the force required to bias the biasable clip 40, may be selected based on the intended design of the apparatus 10, including the desired force in which the biasable clip 40 contacts the plush inner material of the medical cast. Depending on the shape of the biasable clip 40, when the biasable clip 40 is positioned within the annular pocket 30 and in the medical cast 2 (FIGS. 1-2), the biasable clip 40 may contact the plush interior layer of the medical cast around a partial interior circumference of the medical cast, such as is depicted in FIG. 5B.

As shown in FIG. 3B, the biasable clip 40 may have a cross-sectional shape with a concave edge 46 and a convex edge 48, positioned on substantially opposing sides of the biasable clip 40 from one another. When the biasable clip 40 is positioned within the medical cast, or is about to be inserted into the medical cast, the convex edge 48 may be positioned towards the middle of the medical cast while the concave edge 46 may be positioned facing the front terminating end of the medical cast. In this manner, the convex edge 48 may help decrease the necessary force it takes to insert the biasable clip 40 into the cast. When the biasable clip 40 biases outwards, the concave edge 46 can increase the force in which the biasable clip 40 can be pulled out of the interior plush layer of the medical cast, since the concave edge 46 will increase the frictional force against the interior plush layer. Other structural variations on the biasable clip 40 to increase the pull-out resistance of the biasable clip 40 may also be included, such as, for example, surface textures like hooks, barbs, or other the like.

FIGS. 4A-4B are isometric view and detailed view illustrations, respectively, of the biasable clip 40 within the annular pocket 30 of the fabric cover 20 of the medical cast protective structure apparatus 10, in accordance with the first exemplary embodiment of the present disclosure. As shown, the annular pocket 30 is formed along the first end 22 of the fabric cover 20, and the biasable clip 40 is positioned within the annular pocket 30 along the circumference of the fabric cover 20. As shown in the detailed view of FIG. 4B, showing the detail of portion G in FIG. 4A, the annular pocket 30 may have an opening 32 which allows for insertion and removal of the biasable clip 40 within the annular pocket 30. Depending on the specific design of the apparatus 10, it is envisioned that the biasable clip 40 may be affixed, attached, or otherwise secured to the first end 22 of the fabric cover 20 without the need for insertion into an annular pocket 30. For example, the biasable clip 40 could be glued, sewn, or otherwise retained against the first end 22 without being fully encircled by a pocket.

Figure 5A:
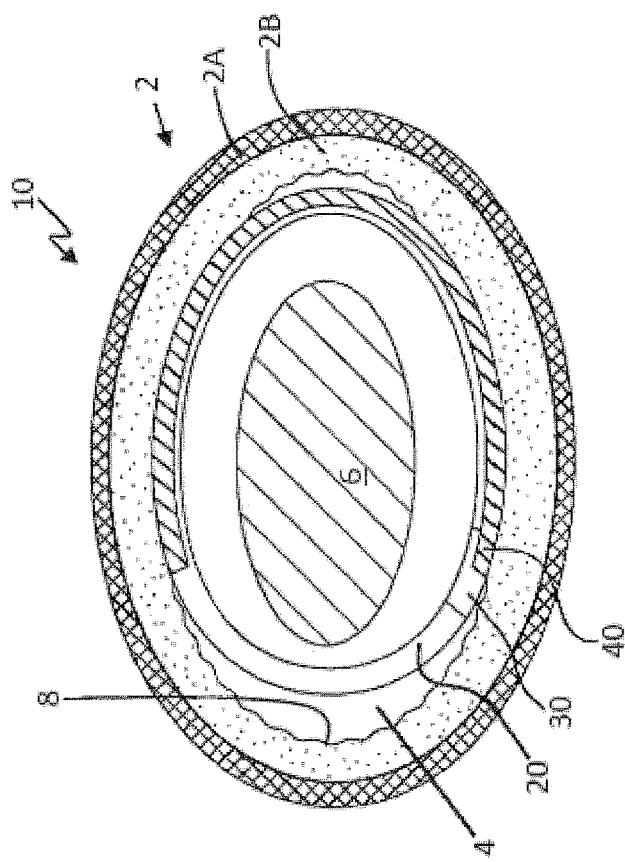
FIGS. 5A-5B are cross-sectional view illustrations of the apparatus with the biasable clip 40 in a collapsed state and an expanded state, respectively, in accordance with the first exemplary embodiment of the present disclosure.
Figure 5B:
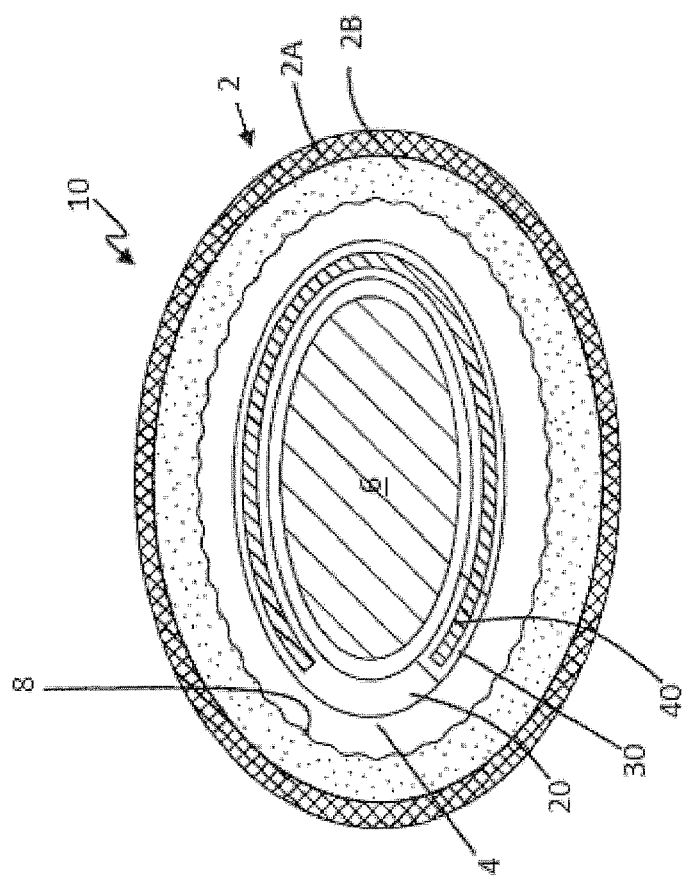

FIGS. 5A-5B are cross-sectional view illustrations of the apparatus 10 with the biasable clip 40 in a collapsed state and an expanded state, respectively, in accordance with the first exemplary embodiment of the present disclosure. As shown in FIG. 5A, the biasable clip 40, positioned within the annular pocket 30 of the fabric cover 20 and positioned about the limb 6 of the patient, is compressed or collapsed so it can be positioned within the medical cast 2. In the collapsed state, the biasable clip 40 may have clearance with fitting in the interior of the medical cast 2, such that it is positioned inwards of the plush cast layers 2B which is surrounded by the rigid cast material 2A. In FIG. 5B, the biasable clip 40 is shown in the expanded or naturally unbiased shape, in which it has forced through the ends of the biasable clip 40 into the plush cast layers 2B. In particular, this positioning of the biasable clip 40 may force the annular pocket 30 of the fabric cover 20 to contact the plush cast material 2B and be pushed or forced at least partially into the plush cast material 2B, to the point where the biasable clip 40 can retain the annular pocket 30 in a substantially stationary position in place within the medical cast 2. This position is shown in FIG. 2. It is noted that FIGS. 5A-5B are not drawn to scale, and that in normal operation, the biasable clip 40 and annular pocket 30 will have tighter tolerances to the patient's limb 6 and the medical cast 2 than depicted in FIGS. 5A-5B.

It is noted that installing the apparatus 10 on a medical cast 2 will customarily involve inverting the fabric cover 20 prior to insertion of the biasable clip 40 and annular pocket 30 into the medical cast 2, such that the length of the fabric cover 20 temporarily covers the patient's hand. Once the biasable clip 40 and annular pocket 30 are positioned in the plush cast material 2B, the fabric cover 20 may be folded back over the exterior of the medical cast 2 to reverse the inversion of the fabric cover 20.

Figure 6:
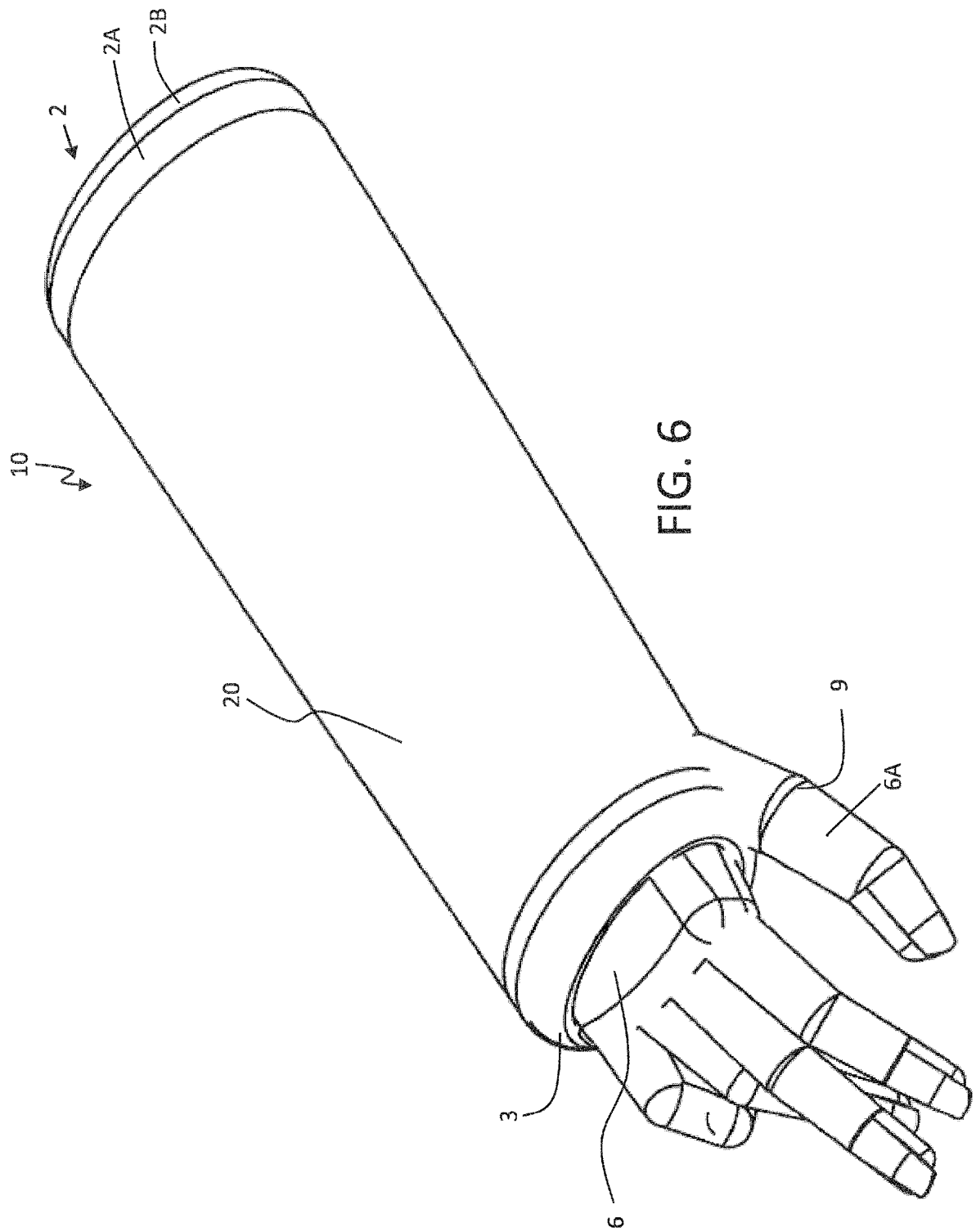
FIG. 6 is an isometric view illustration of the apparatus in use on a medical cast, in accordance with the first exemplary embodiment of the present disclosure.

FIG. 6 is an isometric view illustration of the apparatus 10 in use on a medical cast 2, in accordance with the first exemplary embodiment of the present disclosure. Specifically, FIG. 6 depicts the apparatus 10 in the position after the biasable clip 40 (FIGS. 5A-5B) has been installed within the medical cast 2 and the fabric cover 20 has been slipped over the rigid exterior surface 2A of the medical cast 2. It is noted that the fabric cover 20 may include a hole 9 for the patient's thumb 6A, as shown in FIG. 6. In this position, the fabric cover 20 of the apparatus 10 can effectively cover the medical cast 2, or a substantial portion thereof, to provide a guard from unsanitary contamination of the medical cast 2. If the medical cast 2 is subjected to unsanitary conditions, e.g., in a restroom, the fabric cover 20 can prevent bacteria or other contaminants from gaining access to the medical cast 2. Afterwards, and as desired by the user, the fabric cover 20 can be removed from the medical cast 2 by compressing the biasable clip 40 and removing it from the medical cast 2, and the fabric cover 20 can be washed and/or replaced.

This ability to prevent bacterial contamination to medical casts, especially for children and adolescents who may be unaware of the presence of unsanitary conditions, may provide numerous benefits to the user. For one, the fabric cover 20 can prevent illness and the spread of contaminants by capturing all contaminants on the fabric cover 20, which can then be cleaned easily or replaced with another fabric cover 20. Further, the use of the fabric cover 20 may provide aesthetic improvements to the medical cast. For example, the fabric cover 20 can be colored or designed with pleasing images, such as sports logos, characters, or patterns, and/or the fabric cover 20 may act as a setting for coloring, writing, or other artistry. The apparatus 10 may offer numerous other benefits which may be recognized in the art, all of which are considered within the scope of the present disclosure.

Figure 7:
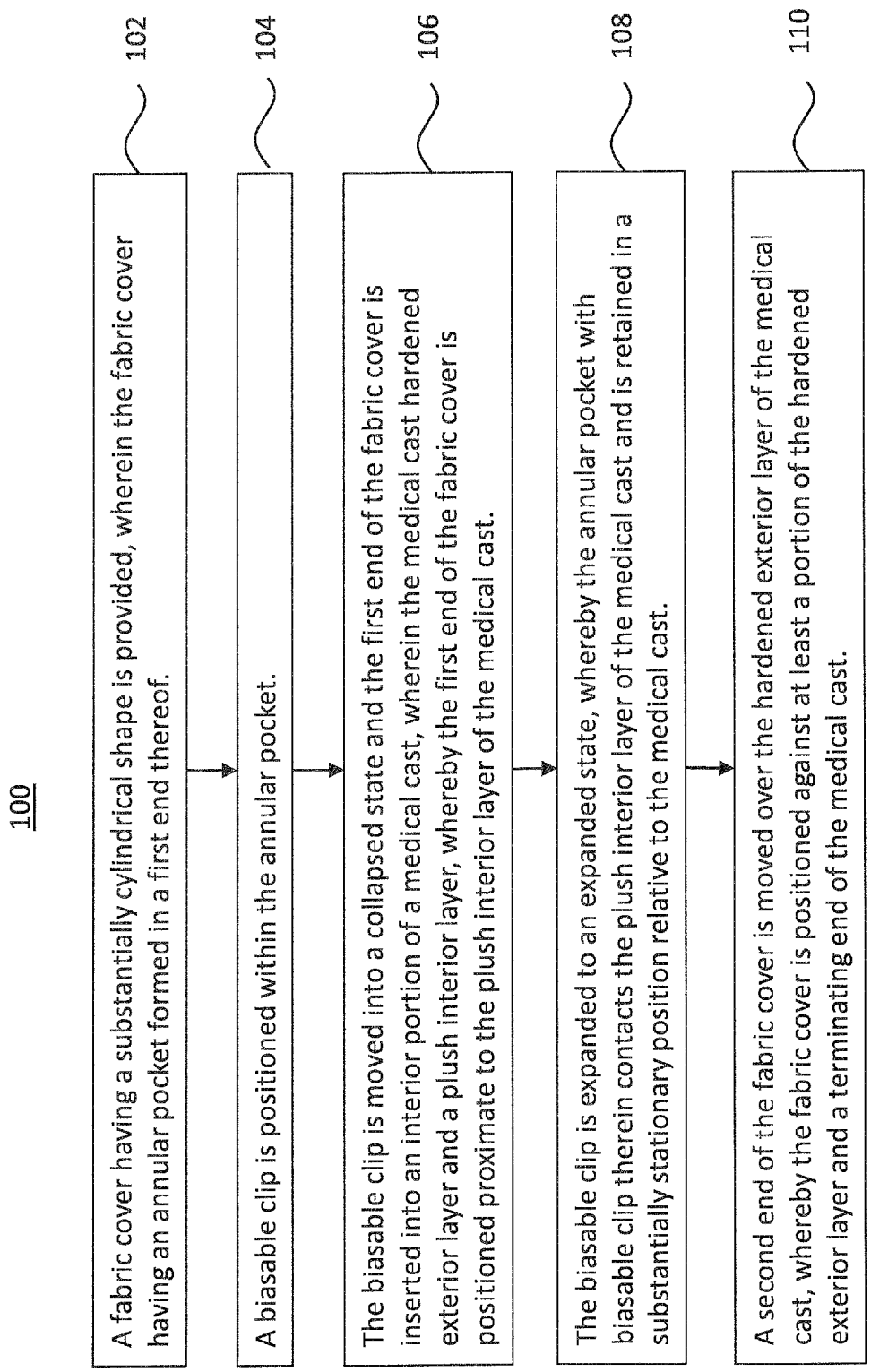
FIG. 7 is a flowchart illustrating a method for applying a protective cover to a medical cast, in accordance with the first exemplary embodiment of the disclosure.

While the specific steps for installing the protective cover over a medical cast may vary, FIG. 7 is a flowchart 100 illustrating a method for applying a protective cover to a medical cast, in accordance with the first exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 102, a fabric cover having a substantially cylindrical shape is provided, wherein the fabric cover having an annular pocket formed in a first end thereof. A biasable clip is positioned within the annular pocket (block 104). The biasable clip is moved into a collapsed state and the first end of the fabric cover is inserted into an interior portion of a medical cast, wherein the medical cast hardened exterior layer and a plush interior layer, whereby the first end of the fabric cover is positioned proximate to the plush interior layer of the medical cast (block 106). The biasable clip is expanded to an expanded state, whereby the annular pocket with biasable clip therein contacts the plush interior layer of the medical cast and is retained in a substantially stationary position relative to the medical cast (block 108). A second end of the fabric cover is moved over the hardened exterior layer of the medical cast, whereby the fabric, cover is positioned against at least a portion of the hardened exterior layer and a terminating end of the medical cast (block 110).

It is noted that the method may include any additional number of steps, functions, and features, including any of those disclosed relative to any other figure herein. For example, moving the biasable clip into the collapsed state further comprises biasing the biasable clip along at least one radii thereof. Contact of the annular pocket with biasable clip therein against the plush interior layer of the medical cast may further comprise at least partially embedding the annular pocket with biasable clip therein within the plush interior layer. A cross-sectional shape of the biasable clip may further comprise the concave edge on a first side of the biasable clip, wherein the first side of the biasable clip is positioned facing the terminating end of the medical cast. Additionally, it is noted that variations on the method for applying the protective structure over the medical cast can include variations in the order of the steps disclosed herein. For example, it is possible that the fabric cover is positioned over the rigid exterior of the medical cast before the biasable clip within the annular pocket of the first of the fabric cover is positioned abutting the plush interior layer of the medical cast. Then, after the annular pocket and biasable clip are retained stationary within the interior plush layer, a position of the remaining body of the fabric cover may be adjusted to provide a snug fit against the medical cast. Other variations, such as supplying fabric covers with biasable clips permanently located within annular pockets, such that users do not need to install the biasable clips themselves, are also considered within the scope of the present disclosure.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claim.

What is claimed is:

1. A medical cast protective structure apparatus comprising:
    a medical cast having a hardened exterior layer and a plush interior layer;
    a water-resistant fabric cover having a substantially cylindrical shape, the fabric cover positioned over at least a portion of an exterior of the medical cast and a terminating end of the medical cast;
    an annular pocket formed in a first end of the fabric cover, wherein the first end of the fabric cover is positioned abutting the plush interior layer of the medical cast; and
    a biasable clip positioned within the annular pocket and oriented along a circumference of the water-resistant fabric cover, wherein the biasable clip is movable between collapsed and expanded states outward about the circumference of the water-resistant fabric cover, wherein in the expanded state, the annular pocket with biasable clip therein contacts the plush interior layer of the medical cast and is retained in a substantially stationary position relative to the medical cast.

2. The apparatus of claim 1, wherein contact by the annular pocket with biasable clip therein and the plush interior layer of the medical cast further comprises the annular pocket being imbedded at least partially within the plush interior layer of the medical cast.

3. The apparatus of claim 1, wherein the biasable clip further comprises at least one of: a substantially circular shape; a wishbone shape; and a horseshoe shape.

4. The apparatus of claim 3, wherein a shape of the biasable clip further comprises at least two sections with a first radii dimension and at least one section with a second radii dimension, wherein the first radii dimension is greater than the second radii dimension.

5. The apparatus of claim 1, wherein the biasable clip contacts the plush interior layer of the medical cast radially around a partial interior circumference of the medical cast.

6. The apparatus of claim 1, wherein a cross-sectional shape of the biasable clip further comprises at least one of: a concave edge; and a convex edge.

7. The apparatus of claim 6, wherein when the cross-sectional shape of the biasable clip further comprises the concave edge on a first side of the biasable clip and the convex edge on a second side of the biasable clip, wherein the first side is substantially opposite the second side, and wherein the concave edge faces the terminating end of the medical cast.

8. The apparatus of claim 1, wherein the annular pocket completely encircles the biasable clip about the circumference of the water-resistant fabric cover, and wherein the annular pocket further comprises an opening therein, wherein the biasable clip is insertable into the annular pocket through the opening.

9. The apparatus of claim 1, wherein the fabric cover further comprises a thumb hole positioned along a forward sidewall thereof.

10. The apparatus of claim 1, wherein the fabric cover is at least partially elastic, whereby the fabric cover is snuggly retained against the portion of an exterior of the medical cast.

11. A medical cast protective structure apparatus comprising:
 a fabric cover having a substantially cylindrical shape;
 an annular pocket formed in a first end of the fabric cover; and
 a biasable clip positionable within the annular pocket and oriented along a circumference of the fabric cover, wherein the annular pocket with the biasable clip positioned therein is insertable into an interior portion of a medical cast with the biasable clip in a collapsed state, wherein after insertion into the interior portion of the medical cast, the biasable clip expands outward about the circumference of the fabric cover to an expanded state to contact an inner surface of the medical cast, wherein the annular pocket with the biasable clip therein is retained in a substantially stationary position relative to the medical cast.

12. The apparatus of claim 11, wherein the biasable clip further comprises at least one of: a substantially circular shape; a wishbone shape; and a horseshoe shape.

13. The apparatus of claim 12, wherein a shape of the biasable clip further comprises at least two sections with a first radii dimension and at least one section with a second radii dimension, wherein the first radii dimension is greater than the second radii dimension.

14. The apparatus of claim 11, wherein the biasable clip is contactable against a plush interior layer of the medical cast radially around a partial interior circumference of the medical cast.

15. The apparatus of claim 11, wherein a cross-sectional shape of the biasable clip further comprises at least one of: a concave edge; and a convex edge.

16. The apparatus of claim 15, wherein when the cross-sectional shape of the biasable clip further comprises the concave edge on a first side of the biasable clip and the convex edge on a second side of the biasable clip, wherein the first side is substantially opposite the second side, and wherein the concave edge faces a terminating end of the medical cast over which the fabric cover is positioned.

* * * * *